US006385280B1

(12) United States Patent
Bittl et al.

(10) Patent No.: US 6,385,280 B1
(45) Date of Patent: May 7, 2002

(54) X-RAY COMPUTED TOMOGRAPHY APPARATUS WITH MODULATION OF THE X-RAY POWER OF THE X-RAY SOURCE

(75) Inventors: Herbert Bittl, Nuremberg; Ernst Neumeier, Aurachtal; Matthias Berger, Forchheim, all of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/370,341

(22) Filed: Aug. 6, 1999

(30) Foreign Application Priority Data

Aug. 18, 1998 (DE) .......................................... 198 37 433
Nov. 2, 1998 (DE) .......................................... 198 50 493

(51) Int. Cl.[7] ................................................ H05G 1/22
(52) U.S. Cl. .......................................... 378/16; 378/106
(58) Field of Search ................................... 378/16, 106

(56) References Cited

U.S. PATENT DOCUMENTS 4,051,377 A * 9/1977 Kemner et al. .............. 378/16
4,174,481 A   11/1979 Liebetruth
4,260,894 A *  4/1981 Neumann .................... 378/16
4,309,614 A    1/1982 Wagner
5,379,333 A    1/1995 Toth
5,450,462 A    9/1995 Toth et al.
5,485,494 A    1/1996 Williams et al.
5,822,393 A   10/1998 Popescu
5,867,555 A    2/1999 Popescu et al.

* cited by examiner

Primary Examiner—Craig E. Church
(74) Attorney, Agent, or Firm—Schiff Hardin & Waite (57) ABSTRACT

An x-ray CT apparatus has an x-ray source which emits an x-ray beam which is displaceable relative to an examination subject, the x-ray source emitting x-rays in the form of one or more pulses during the registration of a projection. An arrangement for modulating the x-ray power sets the duration of the pulses dependent on an angle attenuation profile of the examination subject for the individual projections, such that the mAs product applied for the individual projections correspond to the curve of the angle attenuation profile.

15 Claims, 7 Drawing Sheets

X-RAY COMPUTED TOMOGRAPHY APPARATUS WITH MODULATION OF THE X-RAY POWER OF THE X-RAY SOURCE

BACKGROUND OF THE INVENTION

1. Field of the Invention

The present invention is directed to an x-ray computed tomography (CT) apparatus of the type having means for modulating the x-ray power of an x-ray source that is displaceable relative to an examination subject, and a detector system for the x-rays emanating from the x-ray source.

2. Description of the Prior Art

An x-ray CT apparatus of the above type is disclosed, for example, in U.S. Pat. No. 5,379,333, German OS 195 27 518, German OS195 32 535, German OS 28 15 347 and German OS 198 07 639.

An x-ray CT apparatus generally has an x-ray source that directs a collimated, fan-shaped x-ray beam through the examination subject, for example a patient, onto a single row or multi-row bank of detectors of the detector system. The source and, dependent on the model of x-ray CT apparatus, the detector system as well are mounted on a gantry that rotates around the examination subject. A support table for the examination subject can be moved through the gantry. The position from which the x-rays penetrate the examination subject and the angle at which the x-rays penetrate the examination subject are constantly varied as a result of the rotation of the gantry. Each detector of the detector system produces a signal that represents a measure of the overall transparency of the body of the examination subject for the x-rays emanating from the x-ray source proceeding to the detector. The set of output signals of the detectors of the detector system that is acquired for a specific position of the x-ray source is referred to as a projection. A scan comprises a set of projections that were acquired at various positions of the gantry and/or various positions of the support table. The x-ray CT apparatus registers a number of projections during a scan covering a full revolution of the gantry by 360° around the examination subject in order to be able to construct a two-dimensional tomogram of a slice of the body of the examination subject. More recent CT apparatus simultaneously register a number of slices by employing detector systems having a number of rows of detectors. For each projection, a detector referred to as monitor or reference detector measures the unattenuated intensity of the x-radiation.

There are two systematically different methods for registering the data required for producing CT images of three-dimensional regions of an examination subject.

In conventional scanning, the data are registered during a complete revolution of the gantry and one slice is thus scanned while the examination subject is in a fixed position. The examination subject is moved into a new position between the scanning of successive slices, and the next slice is scanned. This procedure continues until all slices defined by the examination have been scanned.

In a spiral scan, the gantry rotates together with the x-ray source around the examination subject while the support table and the gantry are continuously displaced relative to one another in the direction of the longitudinal axis of the support table. The x-ray tube thus describes a spiral (helical) path with respect to the examination subject until the volume defined by the examination has been scanned. Images of individual slices are then calculated from the spiral data acquired in this way.

In each of these two scan types, the image quality is degraded by quantum noise. The radiation intensity of the x-rays omitted by the x-ray source therefore must be high enough for each projection in order to assure that the minimum radiation intensity of the x-rays emerging from the body of an examination subject and proceeding to a detector will be higher than the noise level.

In known x-ray CT apparatuses with modulation of the x-ray power, the radiation intensity, i.e. the photon flux, is suitably modified as a function of the angular position of the gantry during the scanning of the examination subject in order to process the areas of the examination subject that contain high beam attenuation with the required, high radiation intensity when registering projections, as well as to process the areas of the examination subject that contain lower beam attenuation with correspondingly lower radiation intensity when registering projections, so as to expose the subject to a lower radiation stress.

Such x-ray CT apparatuses, for example, require two orthogonal tomograms (U.S. Pat. No. 4,174,481) or "Scout Views" (U.S. Pat. No. 5,379,333) in order to be able to acquire the information necessary for modulation of the x-ray power with respect to the curve of the maximum beam attenuation value of the individual projections as function of the angular position of the gantry, i.e. with respect to the angle attenuation profile of the examination subject.

To that end, for example, an angle attenuation profile approximated to the actual conditions can be identified from the attenuation information of each line of the tomogram or from the "Scout Views".

The corresponding modulation of the x-ray power ensues by setting the radiation intensity of the x-rays corresponding to the desired x-ray power by modifying the tube current of the x-ray source, namely by influencing the filament current of the glow cathode. Such a setting of the tube current, however, has relatively high inertia (delay) because of the limited heating and cooling rate of the glow cathode, and thus the modulation of the x-ray power can only unsatisfactorily follow angle attenuation profiles having rapid changes of the beam attenuation. Due to an inadequate matching of the modulation of the x-ray power to the angle attenuation profile, additional, even non-uniform image noise therefore occurs.

SUMMARY OF THE INVENTION

An object of the present invention is to provide an x-ray CT apparatus of the species initially described wherein the modulation of the x-ray power is also capable of following rapid changes in the attenuation profile.

This object is inventively achieved in an x-ray CT apparatus having an x-ray source which is displaceable relative to an examination subject and a detector system for the x-rays emanating from the x-ray source, with projections for different positions of the x-ray source, being registered and wherein the x-ray source emits x-rays in one or more pulses during the registration of a projection, and wherein the x-ray power is modulated by setting the duration of the pulses dependent on an attenuation profile of the examination subject for the individual projections such that the mAs product supplied on average for each projection at least qualitatively corresponds to the curve of the attenuation profile.

In a traditional scan, wherein the x-radiation source rotates around the examination subject, and in a spiral scan, where at least the x-ray beam rotates around the subject while a relative displacement between the x-ray source/ detector system and the examination subject in the direction of the axis of the rotation is undertaken, the attenuation profile is in the form of an angle attenuation profile. When, by contrast, a scan is undertaken wherein the rotation of the x-ray beam does not take place and only a relative displacement between the x-ray source/detector system and the examination subject in the direction of the axis of the rotation ensues, the attenuation profile is in the form of an axial attenuation profile, i.e. it reflects the curve of the beam attenuation of the examination subject in the direction of the axis of rotation.

The invention thus is suitable for conventional scanning, spiral scanning and for the registration of so-called topograms.

In the invention, thus, the modulation of the x-ray power does not ensue in such a way that the radiation intensity of the x-radiation is varied via the filament current of the glow cathode but instead the x-ray source emits x-rays in a number of pulses during the registration of a projection, the duration of these pulses being modified for influencing the average x-ray power applied for the registration of the respective projection. By contrast to the influencing of the x-ray power via the filament current of the glow cathode, a modification of the average x-ray power by pulsing the x-radiation is possible practically without inertia, so that the modulation of the x-ray power is capable of following rapid changes in the attenuation profile.

It is advantageous that the radiation intensity need not be modified during a scan; rather, the same radiation intensity can be present in all pulses of a scan, as is preferable, since the momentarily existing x-ray power need not be modified but only the average x-ray power effective during the registration of a projection need be modified by a corresponding setting of the duration of the pulses. At the same time, this offers the advantage that work can always be carried out with a radiation intensity that is adequately high for a good signal-to-noise ratio, possibly even the maximum radiation intensity of the x-ray source, without exposing the subject to an unnecessarily high radiation stress. This is because of the inventive modification of the duration of the pulses in conformity with the attenuation profile. The pulse duration is the determining feature, with a given number of pulses and given tube current, for the mAs product.

Since, due to the pulsing of the x-radiation, the x-ray source is not in operation during the entire time required for acquiring a projection, an improved image resolution is also achieved since, due to the shorter overall time during which the x-ray source is generally active for the registration of a projection, a reduction of the azimuthal smear of the measured values is achieved in conventional scans as well as in spiral scans, this being particularly true for subject regions at greater distances from the rotational axis.

The attenuation profile can be determined in a known way before the actual examination on the basis of topograms or scout views; however, the attenuation profile also can be pre-calculated from projections acquired in the past, using suitable algorithms during the examination.

In a preferred embodiment of the invention, the inventive x-ray CT apparatus has an x-ray source with a vacuum housing in which an anode and an electron emitter for generating an electron beam are accepted, the electron beam striking the anode for generating x-rays, and having a control electrode allocated to the electron emitter, for example a Wehnelt cylinder or a grid, which can be connected by the circuit for modulating the x-ray power to a blocking potential for interrupting the electron beam. The x-ray source is thus constructed analogously to a triode and allows an inertia-free pulsing of the x-rays.

In one version of the invention the circuit for modulating the x-ray power includes a switch for applying the blocking potential, this switch being combined with the x-ray source to form a unit. In this way, the connection between the switch and the control electrode is short, so that disadvantageous influences on the blocking behavior, and thus the pulsing of the x-rays as a result of high capacitance and inductance values of the lines located between the switch and the control electrode are precluded. The switch and x-ray source unit preferably is manufactured by either attaching the switch to the x-ray source, or disposing the switch in the inside of the vacuum housing of the x-ray source.

In a further embodiment of the invention that the circuit for modulating the x-ray power sets the duration of the pulses for each projection such that the mAs product required for adhering to a desired signal-to-noise ratio is achieved for the respective projection. It is assured in this way that a specific signal-to-noise ratio is achieved without administering an unnecessary x-ray dose to the examination subject.

In another embodiment of the invention x-ray CT apparatus has a monitor detector on which the x-rays emanating from the x-ray source are incident unattenuated, and the attenuation profile is calculated using the output signals of the detector system and the monitor detector.

In a preferred embodiment of the invention the circuit or components for the determination of the attenuation profile is/are displaceable relative to the examination subject together with the x-ray source and the detector system. In this case it is not necessary to transmit the data supplied by the detector system and required for the determination of the attenuation profile back and forth between a moving part and a stationary part. Moreover, the image computer is relieved of the task of calculating the attenuation profile, although it of course is possible for the image computer to undertake this task.

DESCRIPTION OF THE PREFERRED EMBODIMENTS

Figure 1:
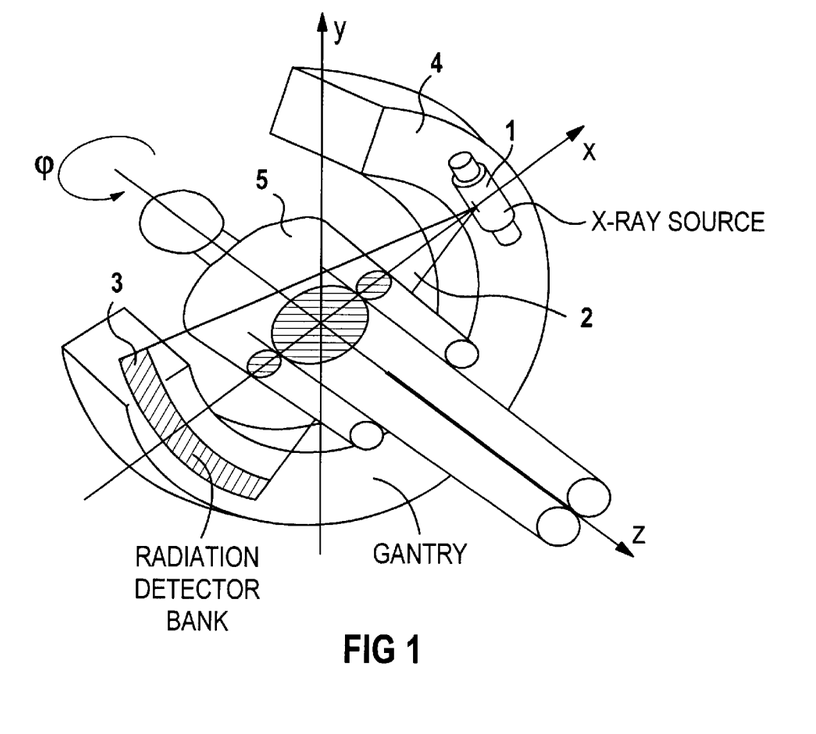
FIG. 1 shows an x-ray CT apparatus as employed for producing cross-sectional images of an examination subject.

The x-ray CT apparatus of the third generation shown in FIG. 1 has an x-ray source 1 that emits a collimated, fan-shaped x-ray beam 2 in the direction onto a detector system including a detector bank 3. The x-ray source 1 and the detector bank 3 are arranged at a rotatable gantry 4 (only partially shown) that can continuously rotate in the φ direction around a patient 5, as the examination subject, and around a rotational axis Z. A monitor detector 6 (see FIG. 7) receives from the x-ray source 1 unattenuated.

In order to register a projection, the x-ray beam 2 penetrates a slice of the patient 5, and the resulting output signals of the individual detectors of the detector bank 3 are acquired by the channels of a data acquisition and measuring system that is not shown in FIG. 1. When, for example, projections at angular spacings of respectively 1° are registered during a complete revolution of the gantry 4 and when the detector bank 3 has, for example, 512 detectors, 360 projections are registered during a complete revolution of the gantry 4, each projection having 512 data entries which the output signals of the detectors that occur during the projection.

When the shoulder area of the patient 5 is registered in a complete revolution of the gantry 4 and when the output signal of that detector that exhibits the smallest output signal is defined for each of the projections, the maximum beam attenuation values $A_{proj\_max}$ of the individual projections can be determined on the basis of the output signal of the monitor detector 6 belonging to the respective projection.

Figure 2:
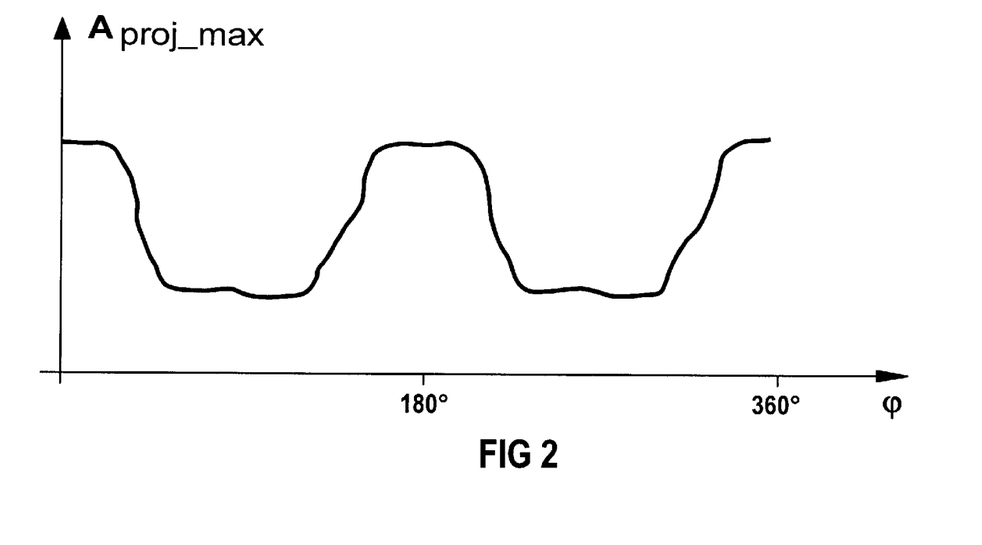
FIG. 2 shows a typical angle attenuation profile for a complete revolution of the x-ray source of the x-ray CT apparatus of FIG. 1 around a human patient in the region of the patient's shoulder.

FIG. 2 shows the maximum beam attenuation values $A_{proj\_max}$ of the individual projections of a complete revolution of the gantry 4 for the shoulder region of a patient as function of the angular position π of the gantry 4, known as the angle attenuation profile. It can be seen that the maximum beam attenuation value $A_{proj\_max}$ fluctuates greatly as a function of the angular position π of the gantry 4.

When, as in a x-ray CT apparatus without dose modulation, x-rays at a constant intensity are employed, which also assures a good image quality for the projection with the highest maximum beam attenuation value $A_{proj\_max}$, a radiation dose is supplied to the patient in the registration of the other projections which have a lower beam attenuation value $A_{proj\_max}$ that is far higher than in the case of an x-ray CT apparatus wherein dose modulation is provided in conformity with the angle attenuation profile of the region of the patient to be examined. Given the inventive x-ray CT apparatus, the dose modulation ensues by pulsing the x-ray emission such that one pulse or a number of pulses occur during the registration of a projection, and by using the duration of the pulses for the individual projections differently corresponding to the angle attenuation profile, namely such that, given projections having a high beam attenuation value $A_{proj\_max}$, the duration of the pulses is longer than in the case of projections having a low beam attenuation value $A_{proj\_max}$.

Figure 3:
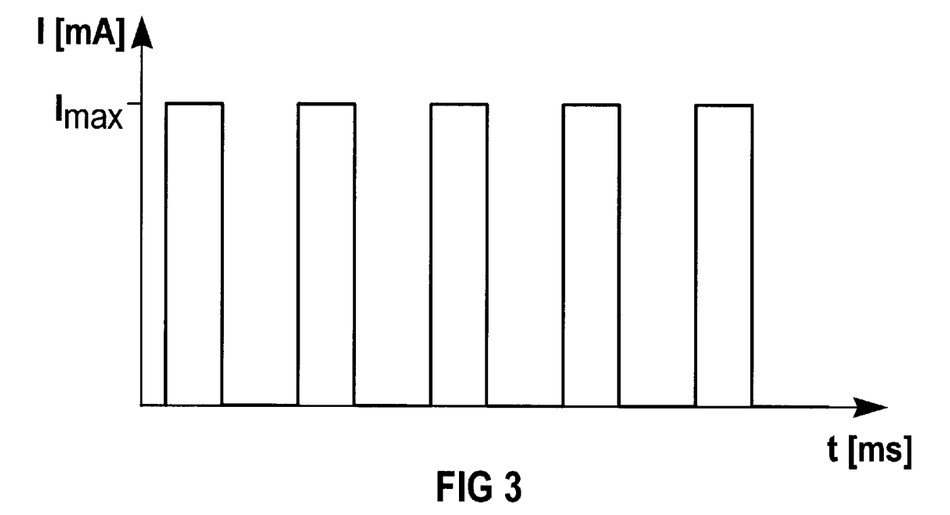
FIGS. 3 and 4 respectively illustrate the pulsed x-rays emitted for the registration of the respective projection for two projections having different maximum beam attenuation.
Figure 4:
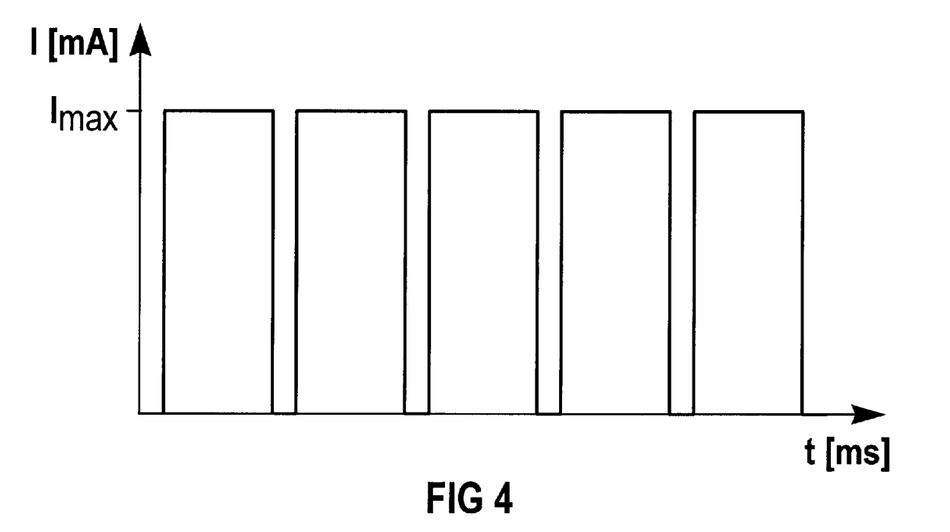

This is illustrated in FIGS. 3 and 4 for the case wherein a number of pulses, for example 5 pulses, are employed for the registration of two different projections. FIG. 4 illustrates the conditions for a higher beam attenuation value, wherein the pulses are approximately twice as long as in the case of FIG. 3 that shows the conditions for a lower beam attenuation value. The intensity of the x-rays $I_R$ is entered over the time t in FIGS. 3 and 4. The overall area of the pulses therefore corresponds to the mAs product applied for registering the respective projection, which is thus approximately twice as high in the case of FIG. 4 as in the case of FIG. 3.

Figure 5:
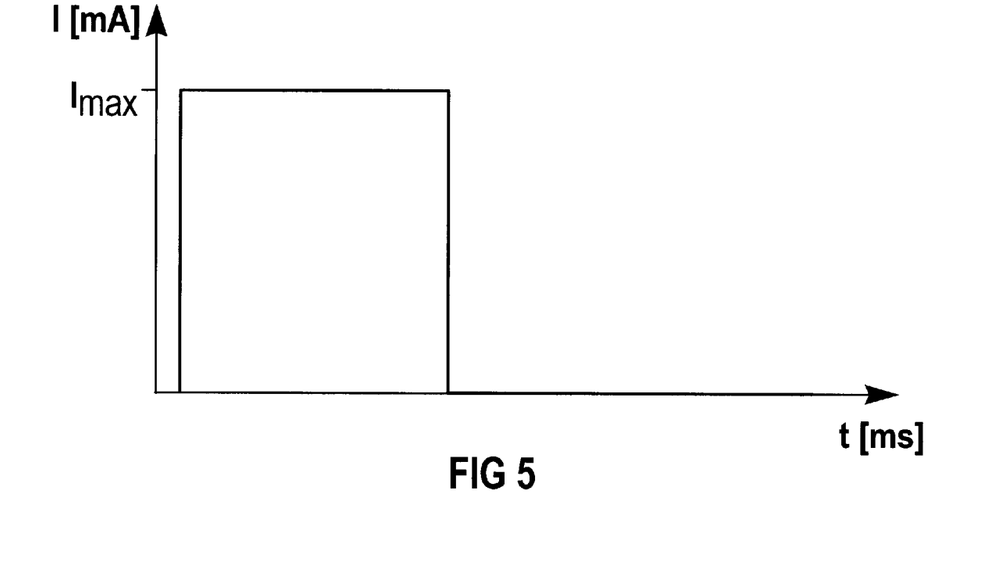
FIGS. 5 and 6, analogous to FIGS. 3 and 4, respectively illustrate the conditions for an operating mode wherein only a single pulse of x-rays is emitted per projection.
Figure 6:
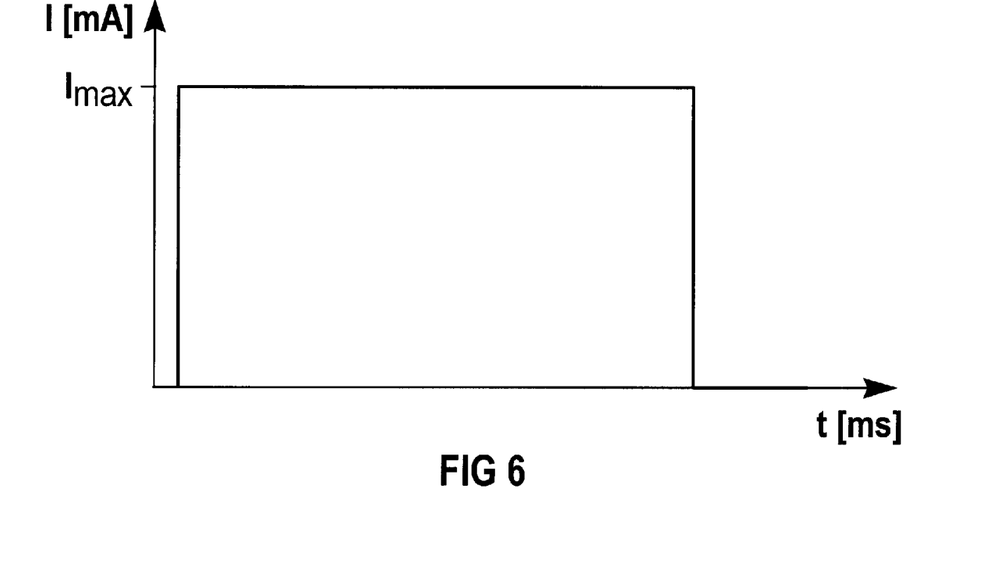

FIGS. 5 and 6 illustrate the registration of the same projections as in the case of FIGS. 3 and 4 for that case wherein only a single pulse is employed for the registration of each of the two projections. The conditions for a higher beam attenuation value are illustrated in FIG. 6 and the duration of the pulses is approximately twice as long as in the case of FIG. 5 wherein the conditions for a lower beam attenuation value are shown.

As a result of pulsing the x-ray emission, the radiation intensity need not be modified for modulation of the x-ray power. On the contrary, all pulses in the registration of a projection exhibit the same radiation intensity, which assures an image quality appropriate for the respective examination instance. Moreover, the same radiation intensity is preferably used during the registration of all projections of a scan. As FIGS. 3 through 6 show as an example, the maximum intensity of the x-rays can be employed in the registration of all projections, which offers the advantage that the maximally possible signal-to-noise ratio is always achieved without stressing the patient 5 with an unnecessarily high radiation dose.

Figure 7:
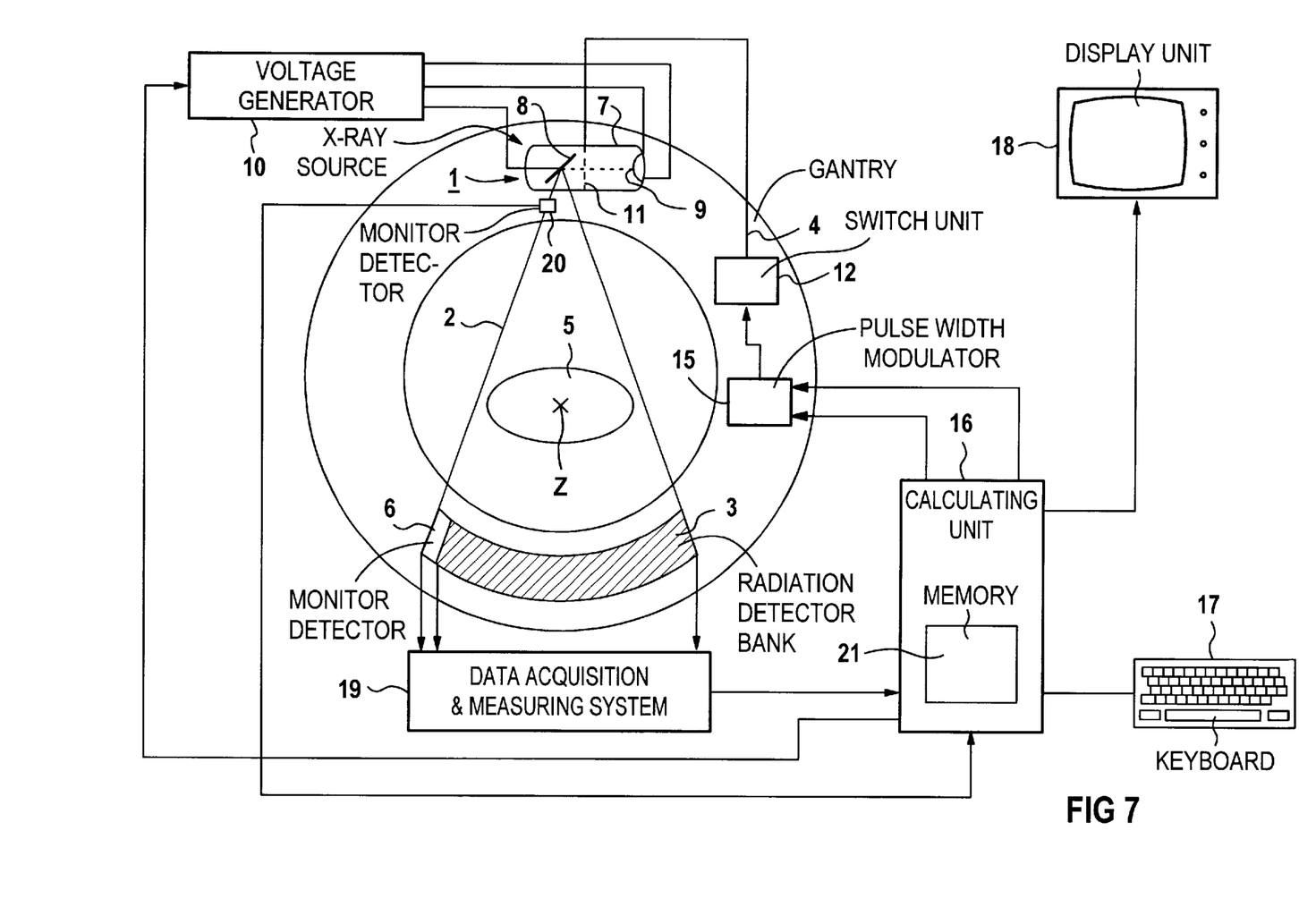
FIG. 7 is a block diagram of the CT apparatus of FIG. 1.

The x-ray CT apparatus according to FIG. 1 is shown in greater detail in FIG. 7. The x-ray source 1 has a vacuum housing 7 in which an anode 8 and a cathode 9, which is a thermionic cathode, are accommodated. The x-ray source 1 is connected to an electrical generator circuit 10 that provides the voltages required for the operation of the x-ray source, namely the tube voltage $U_R=U++U-$ between the anode 8 and the cathode 9, and the filament voltage $U_H$ across the cathode 9. An electron beam that strikes the anode 8 and from which the x-ray beam 2 in turn emanates proceeds from the cathode 9 during operation of the x-ray source 1, as indicated with dot-dash lines in FIG. 7. A control electrode is arranged between the cathode 9 and the anode 8, this being fashioned as grid 11 in the exemplary embodiment according to FIGS. 1 and 7.

A blocking potential can be applied to the grid 11 with a switch unit 12. Dependent on the signal at a control input of the switch unit 12, the grid 11 is separated from the blocking potential, thereby allowing the electron beam to proceed to the anode 8, or is connected to the blocking potential, this being dimensioned such that, when the grid 11 is at blocking potential, the electrons are prevented from proceeding from the cathode 9 to the anode 8. It is thus possible to pulse the x-radiation with the grid 11 and the switch unit 12.

For forming a unitary assembly with the x-ray source 1, the switch unit 12 and the pulse width modulator 15, just like the x-ray source 1, are directly attached to the gantry 4, so that the connection of the switch unit 12 to the grid 11 is short, and consequently low-capacitance and low-inductance.

The switch unit 12 has a control input that is connected to the output of a pulse width modulator 15. In the described exemplary embodiment, an electronic calculating unit 16 serves both as the control unit for the x-ray CT apparatus and as the computer, and is stationary, i.e. not attached to the gantry 4. The calculating unit 16 supplies the pulse width modulator 15 with, first, a clock signal and, second, a signal that serves the purpose of setting the pulse duration of pulses occurring at the output of the pulse width modulator 15 synchronously with the clock signal. These output pulses are supplied to the control input of the switch unit 12 and thus set the duration of the pulses of x-rays.

A keyboard 17 and a display unit 18, for example a monitor, are connected to the electronic calculating unit 16. The keyboard 17 allows an operator to operate the x-ray CT apparatus. The display unit 18 serves the purpose of displaying images produced with the x-ray CT apparatus.

A data acquisition and measuring system 19 is also connected to the electronic calculating unit 16, the detectors of the detector bank 3 that are attached to the gantry 4 lying opposite the x-ray source 1 being connected to the input channels of this system 19. The aforementioned monitoring detector 6 is connected to a special monitor channel of the data acquisition and measuring system 19 that is attached to the gantry 4 and thus rotates in common with the detector bank 3.

In the described exemplary embodiment, the clock signal supplied to the pulse width modulator 15 is synchronized with the working clock of the data acquisition and measuring system 19, so that a proper function is assured even when operation takes place with only one pulse of x-rays per projection. When a number of pulses of x-rays are used per projection, this synchronization is not absolutely necessary but is advantageous for the image reconstruction.

The electronic calculating unit 16 contains a memory 21 in which one or more angle attenuation profiles of the patient 5 to be examined are stored, these having been determined before the actual examination on the basis of topograms or scout views in a known way. On the basis of the angle attenuation profile applicable to the region of the patient 5 being scanned, the electronic calculating unit 16 changes the control signal supplied to the pulse width modulator 15 such that the mAs product that is applied to the patient 5 for the registration of the respective projection assures that the image noise does not exceed a specific value, that can be preselected via the keyboard 17.

The angle attenuation profile need not necessarily be acquired from topograms or scout views registered before the actual examination and stored in the memory 21, but, in an alternative operating mode, can be acquired during the actual examination, "on line" so to speak, by extrapolating, in the calculating unit 16, the beam attenuation value of the angle attenuation profile belonging to the next projection to be registered, from the data of a number of projections registered immediately before and the appertaining data of the monitor detector 6 as well as data from a further monitor detector 20 attached in the region of the x-ray source, the monitor detector 20 being connected to the electronic calculating unit 16. This extrapolation can begin as soon as a certain number of projections, for example the number corresponding to half a revolution of the gantry 4, was registered with a permanent prescribed duration of the pulses, for example the maximum duration of the pulses.

In the exemplary embodiment according to FIGS. 1 and 7, the switch unit 12 and the pulse width modulator 15, like the x-ray source 1, are attached in common on the gantry 4, so that these components are combined to form a unit, and thus the connection of the switch unit 12 to the grid 11 is short and, accordingly, is low in capacitance and low in inductance. To achieve a structure that is even lower in inductance and capacitance, however, as shown in FIG. 8 the x-ray source, the switch unit and the pulse width modulator are directly combined to form a single structural unit.

Figure 8:
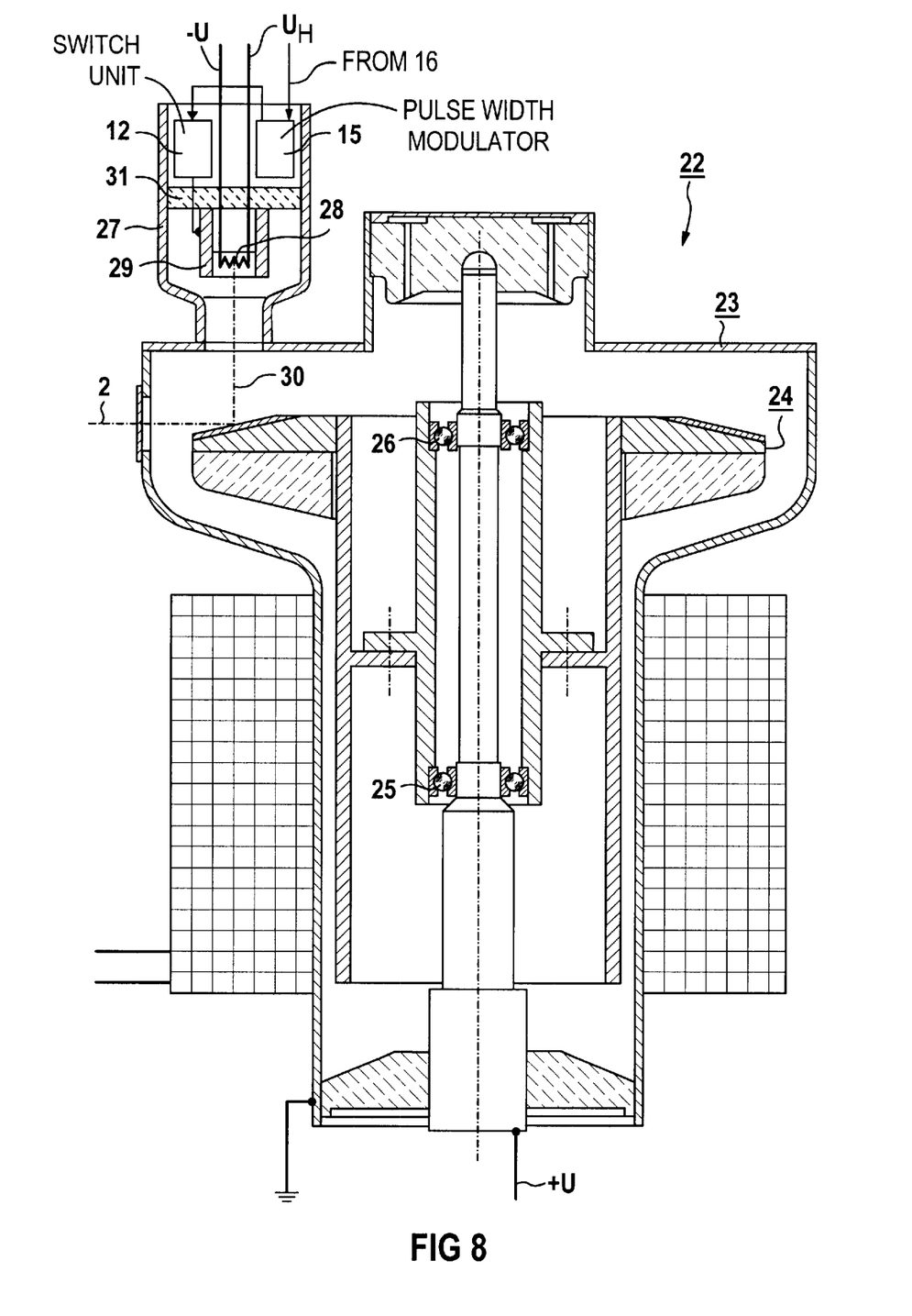
FIGS. 8 and 9 respectively show versions of the x-ray source suitable for the x-ray CT apparatus according to FIGS. 1 and 5.

As can be seen from FIG. 8, the x-ray source 22 has a vacuum housing 23 in which a rotating anode 24 is rotatably seated with two roller bearings 25 and 26. The vacuum housing 22 has a shoulder 27 in which a cathode 28, such as a thermionic cathode, is accepted.

Differing from the x-ray source according to FIG. 7, the cathode 28 does not have a grid allocated to it as a control electrode but instead has a Wehnelt electrode 29, so that the electron beam 30 emanating from the cathode 28 during operation of the x-ray source 22 can be interrupted as needed by connecting the Wehnelt electrode 29 to the pulse width modulator 15 via the switch unit 12. The switch unit 12 as well as the pulse width modulator 15 are accepted in the shoulder 27 of the vacuum housing 23 for forming a structural unit, namely outside the vacuum space which, in the exemplary embodiment according to FIG. 8, is limited by an insulator 31 carrying the cathode 28 and the Wehnelt electrode 29.

Figure 9:
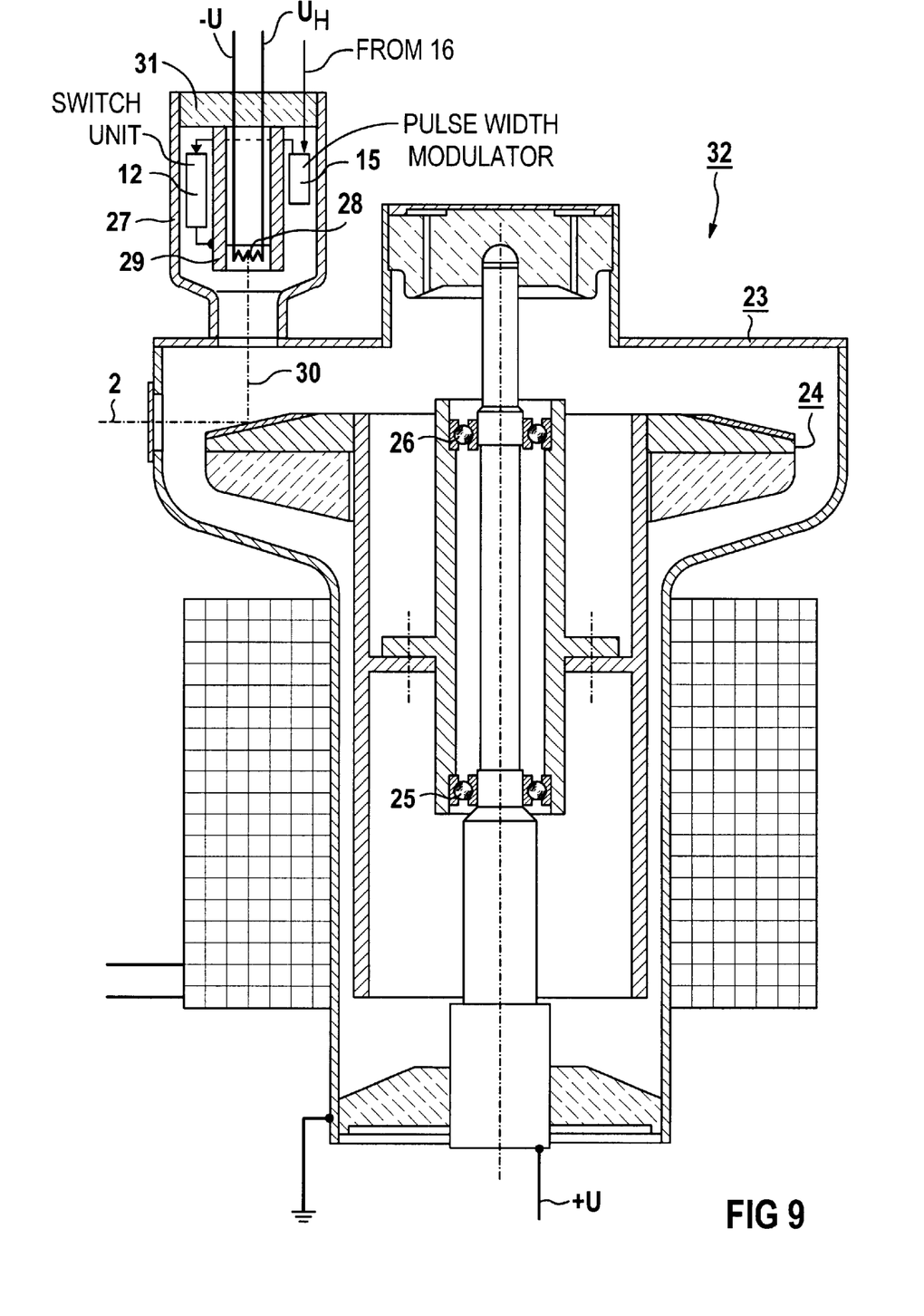

For achieving a structure that is even lower in inductance and capacitance, there is also the possibility of manufacturing the structural unit including the x-ray source, switch unit and pulse width modulator by accommodating—as schematically indicated in FIG. 9—the switch unit 12 and the pulse width modulator 15 inside the vacuum housing 23 of the x-ray source 32, that otherwise corresponds to that of FIG. 8. This procedure assumes that the switch unit 12 and the pulse width modulator 15 are constructed of vacuum-compatible components or are hermetically tightly encapsulated.

An operating mode is described above wherein a single slice of the patient 5 is scanned. In another operating mode, the gantry 4 and the patient 5 are shifted relative to one another in the direction of the rotational axis z, so that three-dimensional regions of the patient 5 are scanned, either by successive scanning of planar slices or by spiral scanning.

In a further operating mode, the rotation of the gantry 4 is blocked and the gantry 4 and the patient 5 are shifted relative to one another in the direction of the rotational axis z in order to be able to register as topograms. In this case as well, a pulsing of the x-rays ensues by adapting the duration of the pulses to, in this case, an axial attenuation profile, which is preferably determined by extrapolation in the electronic calculating unit 16, analogously to the extrapolation described above for the rotating gantry 4.

Moreover, the storage of the attenuation profiles can ensue in the pulse width modulator 15, or the pulse width modulator 15 can undertake the extrapolation of the attenuation profile. The pulse width modulator 15 is then supplied with the required data by the electronic calculating unit 16.

Figure 10:
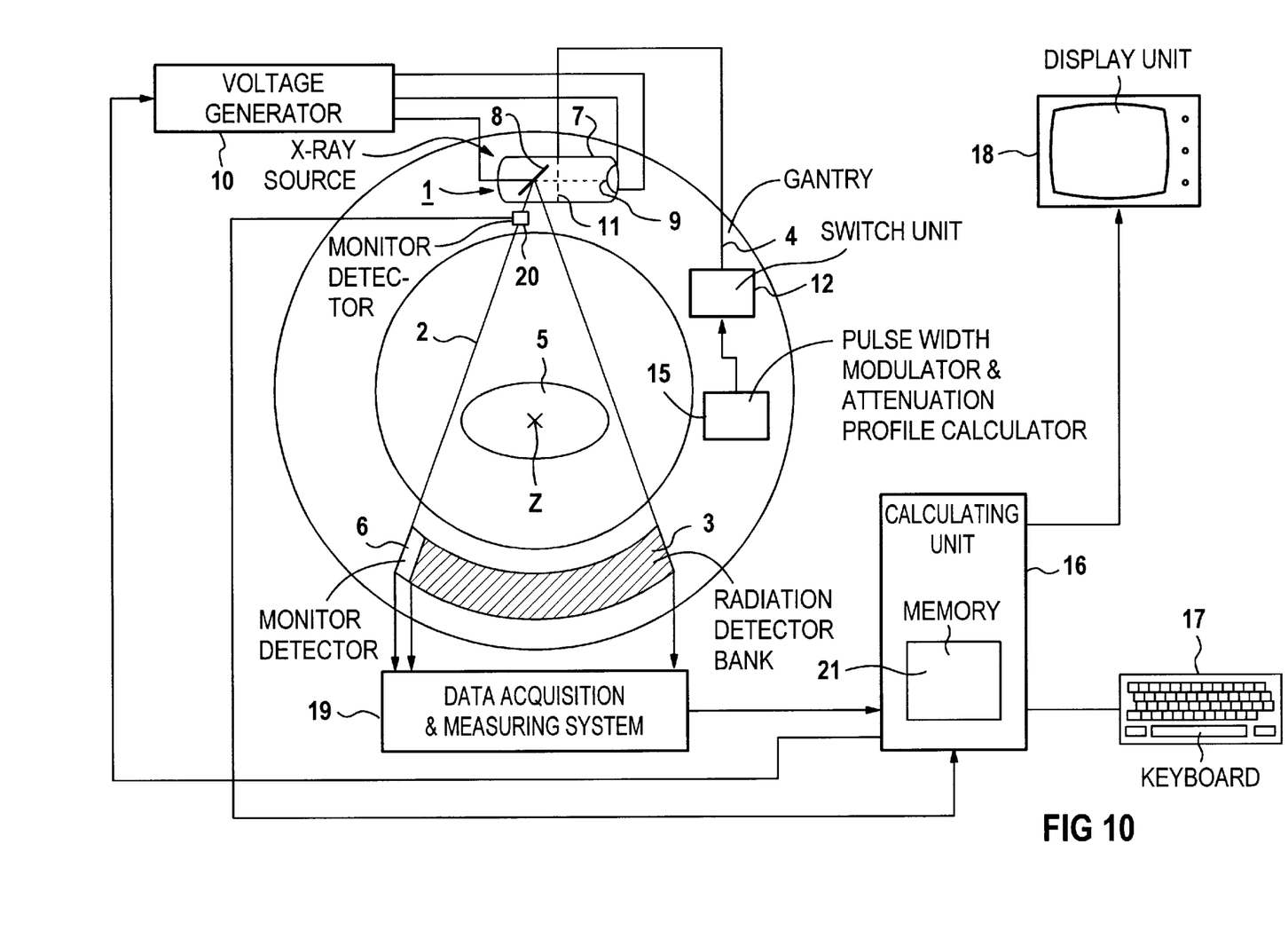
FIG. 10 is a block diagram of a further embodiment of the inventive CT apparatus.

The exemplary embodiment according to FIG. 10 differs from that described above in that the pulse width modulator 15a in this version also completely determines the attenuation profile which is to be taken into consideration, but it does not receive the data required for this purpose from the electronic calculating unit 16 but instead receives the data directly from the data acquisition and measuring system 19, this being illustrated in FIG. 10 by a corresponding line. As a result, the transmission of data from the stationary electronic calculating unit 16 to the pulse width modulator 15 located on the gantry 4, that is required in the case of the above-described exemplary embodiment is avoided. Additionally, the electronic calculating unit 16 is relieved of this task, so that it can satisfy its other jobs, for example the image reconstruction, correspondingly faster.

In the case of the described exemplary embodiments, the detector has a single line of detector elements. The invention, however, also can be employed in conjunction with an x-ray CT apparatus with a detector formed by a number of lines of detector elements, which allows a number of projections to be simultaneously registered.

The x-ray source of the inventive x-ray CT apparatus can be an x-ray tube of any of a variety of types, for example a fixed anode tube as in the case of the exemplary embodiment according to FIGS. 1 and 7, a rotating anode tube as in the case of the exemplary embodiments according to FIGS. 8 and 9 or known rotary bulb radiators. It is only important that x-ray pulsing capability be available. Differing from the exemplary embodiments described above, the pulsing of the x-rays need not ensue with a control electrode that blocks the electron flow, but can ensue in some other way, for example by pulsing the tube voltage.

The invention has been described above with reference to the example of an x-ray CT apparatus of the third generation, however, it can also be employed in an x-ray CT apparatus of the fourth generation, wherein an annular, stationary detector bank is provided instead of the detector bank revolving around the examination subject together with the x-ray source.

Although the invention has been described with reference to the example of a medical application, it can also be employed in non-medical fields.

Although modifications and changes may be suggested by those skilled in the art, it is the intention of the inventors to embody within the patent warranted hereon all changes and modifications as reasonably and properly come within the scope of our contribution to the art.

We claim as our invention:

1. An x-ray computed tomography apparatus comprising:
   an x-ray source which emits an x-ray beam, said x-ray beam being displaceable relative to an examination subject having an attenuation profile, to irradiate said examination subject from a plurality of different positions, said x-ray beam having an x-ray power associated therewith;
   a radiation detector on which said x-ray beam is incident, said detector producing measurement data dependent on attenuation of said x-ray beam by said subject for a plurality of projections corresponding to respectively different positions of said x-ray beam;
   a pulsing arrangement in communication with said x-ray source to cause said x-ray beam to be emitted in at least one pulse of x-rays during acquisition of the measurement data for each projection; and
   a modulation arrangement for modulating the x-ray power by setting a duration of said at least one pulse dependent on said attenuation profile during each projection to produce an mAs product to achieve a selected signal-to-noise ratio in each projection and so that an average of said mAs product substantially corresponds to said attenuation profile in each projection.

2. A computed tomograph apparatus as claimed in claim 1 wherein said x-ray beam is displaceable around said examination subject, and wherein said attenuation profile comprises an angle attenuation profile.

3. A computed tomography apparatus as claimed in claim 2 wherein said x-ray beam is rotatable around said examination subject around an axis of rotation, and further comprising means for producing a relative displacement between said x-ray beam and said radiation detector, and said examination subject, along said axis of rotation.

4. A computed tomography apparatus comprising:
   an x-ray source comprising a vacuum housing containing an anode and an electron emitter which emits an electron beam, said electron beam striking said anode to generate an x-ray beam, and a control electrode disposed to interact with said electron beam between said emitter and said anode, said x-ray beam being displaceable relative to an examination subject having an attenuation profile, to irradiate said examination subject from a plurality of different positions, said x-ray beam having an x-ray power associated therewith;
   control circuitry connected to said control electrode for applying a blocking electrical potential to said control electrode to interrupt said electron beam to modulate said x-ray power, said control circuitry including a switch for connecting and disconnecting said control electrode to a voltage supply, said switch being combined with said x-ray source to form a single unit therewith;
   a radiation detector on which said x-ray beam is incident, said detector producing measurement data dependent on attenuation of said x-ray beam by said subject for a plurality of projections corresponding to respectively different positions of said x-ray beam;
   a pulsing arrangement in communication with said x-ray source to cause said x-ray beam to be emitted in at least one pulse of x-rays during acquisition of the measurement data for each projection; and
   a modulation arrangement for modulating the x-ray power by setting a duration of said at least one pulse dependent on said attenuation profile during each projection so that an average mAs product substantially corresponds to said attenuation profile.

5. A computed tomography apparatus as claimed in claim 4 wherein said x-ray beam and said radiation detector are rotatable around said examination subject around an axis of rotation, and further comprising means for producing a relative displacement between said x-ray beam and said radiation detector, and said examination subject, along said axis of rotation, and wherein said attenuation profile comprises an axial attenuation profile along said axis of rotation.

6. A computed tomography apparatus as claimed in claim 4 wherein said control electrode comprises a Wehnelt electrode.

7. A computed tomography apparatus as claimed in claim 4 wherein said control electrode comprises a grid.

8. A computed tomography apparatus as claimed in claim 4 wherein said x-ray source is displaceable relative to said examination subject to displace said x-ray beam relative to said examination subject, and further comprising a calculation unit wherein said attenuation profile is calculated, said calculation unit being displaceable relative to said examination subject in common with said x-ray source.

9. A computed tomography apparatus as claimed in claim 4 wherein said x-ray source is displaceable relative to said examination subject to displace said x-ray beam relative to said examination subject, and wherein said switch is displaceable in common with said x-ray source relative to said examination subject.

10. A computed tomography apparatus as claimed in claim 4 wherein said switch is attached to said x-ray source.

11. A computed tomography apparatus as claimed in claim 4 wherein said switch is contained inside said vacuum housing of said x-ray source.

12. A computed tomography apparatus as claimed in claim 4 wherein said x-ray source has a high voltage connection including a plug and a cable, and wherein said switch is integrated in one of said plug and said cable.

13. A computed tomography apparatus as claimed in claim 4 wherein said modulating arrangement modulates said x-ray power to produce a mAs product to achieve a selected signal-to-noise ratio in each projection.

14. A computed tomography apparatus as claimed in claim 4 further comprising a monitor detector, on which a portion of said x-ray beam is incident without attenuation by said subject, said monitor detector producing a monitor detector output dependent on the x-rays incident thereon, and a calculation unit supplied with said monitor detector output and supplied with at least some of said measurement data, for determining said attenuation profile from said monitor detector output and said at least some of said measurement data.

15. An x-ray computed tomography apparatus comprising:
   an x-ray source which emits an x-ray beam, said x-ray source being displaceable relative to an examination subject having an attenuation profile, to displace said x-ray beam to irradiate said examination subject from a plurality of different positions, said x-ray beam having an x-ray power associated therewith;
   a radiation detector on which said x-ray beam is incident, said detector producing measurement data dependent on attenuation of said x-ray beam by said subject for a plurality of projections corresponding to respectively different positions of said x-ray beam;
   a pulsing arrangement in communication with said x-ray source to cause said x-ray beam to be emitted in at least one pulse of x-rays during acquisition of the measurement data for each projection;
   a modulation arrangement for modulating the x-ray power by setting a duration of said at least one pulse dependent on said attenuation profile during each projection so that an average mAs product substantially corresponds to said attenuation profile; and
   a calculation unit wherein said attenuation profile is calculated, said calculation unit being displaceable relative to said examination subject in common with said x-ray source.

* * * * *